(12) United States Patent
Lubock

(10) Patent No.: US 8,398,535 B2
(45) Date of Patent: *Mar. 19, 2013

(54) CATHETER ASSEMBLY FOR DELIVERING A RADIATION SOURCE INTO A BODY CAVITY

(75) Inventor: Paul Lubock, Laguna Niguel, CA (US)

(73) Assignee: Senorx, Inc., Tempe, AZ (US)

( * ) Notice: Subject to any disclaimer, the term of this patent is extended or adjusted under 35 U.S.C. 154(b) by 10 days.

This patent is subject to a terminal disclaimer.

(21) Appl. No.: 13/053,262

(22) Filed: Mar. 22, 2011

(65) Prior Publication Data

US 2011/0172485 A1 Jul. 14, 2011

Related U.S. Application Data

(60) Division of application No. 11/155,789, filed on Jun. 17, 2005, now Pat. No. 7,935,044, which is a continuation of application No. 10/290,002, filed on Nov. 6, 2002, now Pat. No. 6,923,754.

(51) Int. Cl.
*A61N 5/00* (2006.01)
(52) U.S. Cl. .......................................................... 600/3
(58) Field of Classification Search .................. 600/1–8
See application file for complete search history.

(56) References Cited

U.S. PATENT DOCUMENTS

| | | |
|---|---|---|
| 3,324,847 A | 6/1967 | Zoumboulis |
| 3,872,856 A | 3/1975 | Clayton |
| 3,975,350 A | 8/1976 | Hudgin et al. |
| 4,119,094 A | 10/1978 | Micklus et al. |
| 4,454,106 A | 6/1984 | Gansow et al. |
| 4,571,241 A | 2/1986 | Christopher |
| 4,690,677 A | 9/1987 | Erb |
| 4,763,642 A | 8/1988 | Horowitz |
| 4,929,470 A | 5/1990 | Rittenhouse et al. |
| 4,998,917 A | 3/1991 | Gaiser et al. |
| 4,998,930 A | 3/1991 | Lundahl |
| 5,059,166 A | 10/1991 | Fischell et al. |
| 5,106,360 A | 4/1992 | Ishiwara et al. |
| 5,167,622 A | 12/1992 | Muto |
| 5,199,939 A | 4/1993 | Dake et al. |
| 5,227,969 A | 7/1993 | Waggener et al. |
| 5,259,847 A | 11/1993 | Trambert |
| 5,302,168 A | 4/1994 | Hess |

(Continued)

FOREIGN PATENT DOCUMENTS

| | | |
|---|---|---|
| EP | 0536440 A1 | 4/1993 |
| EP | 0642766 A2 | 3/1995 |

(Continued)

OTHER PUBLICATIONS

*Hologic, Inc., CYTYC Corp.*, and *Hologic L.P. v. Senorx, Inc.*; Northern District of California, San Jose Division, Case No. 08-CV-0133 RMW, Defendant Senorx, Inc.'s Notice of Motion and Motion for Summary Udgment of Invalidity ('142 Patent, Claims 1 & 8) and Non-Infringement ('813 Patent, Claims 11 & 12; '204 Patent, Claims 4 & 17), filed May 20, 2009, pp. 7-22, discussing Ashpole, et al., A New Technique of Brachytherapy for Malignant Gliomas with Caesium-137: A New Method for Utilizing a.

(Continued)

*Primary Examiner* — John Lacyk

(57) ABSTRACT

A catheter assembly for delivering a radiation source into a body cavity includes a catheter shaft having a distal end and a proximal end. An inflatable balloon is coupled to the catheter shaft between the distal end and the proximal end. A dose delivery lumen extends along the catheter shaft between the proximal end and the distal end. The dose delivery lumen is configured to receive the radiation source. A radioabsorptive portion is surrounded by the inflatable balloon.

18 Claims, 5 Drawing Sheets

U.S. PATENT DOCUMENTS

| | | | |
|---|---|---|---|
| 5,312,356 A | 5/1994 | Engelson et al. |
| 5,314,518 A | 5/1994 | Ito et al. |
| 5,342,305 A | 8/1994 | Shonk |
| 5,381,504 A | 1/1995 | Novack et al. |
| 5,411,466 A | 5/1995 | Hess |
| 5,417,687 A | 5/1995 | Nardella et al. |
| 5,428,658 A | 6/1995 | Oettinger et al. |
| 5,429,582 A | 7/1995 | Williams |
| 5,503,613 A | 4/1996 | Weinberger |
| 5,535,817 A | 7/1996 | Dunne |
| 5,566,221 A | 10/1996 | Smith et al. |
| 5,603,991 A | 2/1997 | Kupiecki et al. |
| 5,611,767 A | 3/1997 | Williams |
| 5,616,114 A | 4/1997 | Thornton et al. |
| 5,621,780 A | 4/1997 | Smith et al. |
| 5,653,683 A | 8/1997 | D'Andrea |
| 5,662,580 A | 9/1997 | Bradshaw et al. |
| 5,704,926 A | 1/1998 | Sutton |
| 5,720,717 A | 2/1998 | D'Andrea |
| 5,759,173 A | 6/1998 | Preissman et al. |
| 5,782,742 A | 7/1998 | Crocker et al. |
| 5,820,594 A | 10/1998 | Fontirroche et al. |
| 5,820,717 A | 10/1998 | Siegenthaler |
| 5,863,285 A | 1/1999 | Coletti |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,993,972 A | 11/1999 | Reich et al. |
| 6,022,308 A | 2/2000 | Williams |
| 6,033,357 A | 3/2000 | Ciezki et al. |
| 6,036,631 A | 3/2000 | McGrath et al. |
| 6,083,148 A | 7/2000 | Williams |
| 6,086,970 A | 7/2000 | Ren |
| 6,093,142 A | 7/2000 | Ciamacco, Jr. |
| 6,095,966 A | 8/2000 | Chornenky et al. |
| 6,143,013 A | 11/2000 | Samson et al. |
| 6,200,257 B1 | 3/2001 | Winkler |
| 6,217,565 B1 | 4/2001 | Cohen |
| 6,251,059 B1 | 6/2001 | Apple et al. |
| 6,256,529 B1 | 7/2001 | Holupka et al. |
| 6,282,142 B1 | 8/2001 | Miyawaki |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,413,203 B1 | 7/2002 | Sahatjian |
| 6,413,204 B1 | 7/2002 | Winkler et al. |
| 6,416,492 B1 | 7/2002 | Nielson |
| 6,458,069 B1 | 10/2002 | Tam et al. |
| 6,482,142 B1 | 11/2002 | Winkler et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,605,030 B2 | 8/2003 | Weinberger |
| 6,610,013 B1 | 8/2003 | Fenster et al. |
| 6,615,070 B2 | 9/2003 | Lee |
| 6,673,006 B2 | 1/2004 | Winkler |
| 6,706,014 B2 | 3/2004 | Banik et al. |
| 6,723,052 B2 | 4/2004 | Mills |
| 6,746,392 B2 | 6/2004 | Stiger et al. |
| 6,752,752 B2 | 6/2004 | Geitz |
| 6,770,058 B1 | 8/2004 | Liprie |
| 6,913,600 B2 | 7/2005 | Valley et al. |
| 6,955,641 B2 * | 10/2005 | Lubock ............................ 600/3 |
| 6,983,754 B1 | 1/2006 | Anderson et al. |
| 7,098,463 B2 | 8/2006 | Adamovics |
| 7,107,089 B2 | 9/2006 | Lee |
| 7,171,255 B2 | 1/2007 | Holupka et al. |
| 7,201,715 B2 | 4/2007 | Burdette et al. |
| 7,322,929 B2 | 1/2008 | Lovoi |
| 7,404,791 B2 | 7/2008 | Linares et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,662,082 B2 | 2/2010 | White et al. |
| 7,783,006 B2 | 8/2010 | Stewart et al. |
| 7,885,382 B2 | 2/2011 | Stewart et al. |
| 7,887,476 B2 | 2/2011 | Hermann et al. |
| 7,935,044 B2 * | 5/2011 | Lubock ............................ 600/3 |
| 2001/0049464 A1 | 12/2001 | Ganz |
| 2001/0051669 A1 | 12/2001 | McGhee |
| 2002/0045893 A1 | 4/2002 | Lane et al. |
| 2002/0055666 A1 | 5/2002 | Hunter et al. |
| 2002/0095114 A1 | 7/2002 | Palasis |
| 2002/0177804 A1 | 11/2002 | Saab |
| 2003/0144570 A1 | 7/2003 | Hunter et al. |
| 2004/0039437 A1 | 2/2004 | Sparer et al. |
| 2004/0054366 A1 | 3/2004 | Davison et al. |
| 2004/0116767 A1 | 6/2004 | Lebovic et al. |
| 2005/0061771 A1 | 3/2005 | Murphy |
| 2005/0080313 A1 | 4/2005 | Stewart et al. |
| 2005/0101823 A1 | 5/2005 | Linares et al. |
| 2005/0124843 A1 | 6/2005 | Singh |
| 2005/0240073 A1 | 10/2005 | Apffelstaedt et al. |
| 2005/0277577 A1 | 12/2005 | Hunter et al. |
| 2006/0020156 A1 | 1/2006 | Shukla |
| 2006/0020256 A1 | 1/2006 | Bell et al. |
| 2006/0100475 A1 | 5/2006 | White et al. |
| 2006/0116546 A1 | 6/2006 | Eng |
| 2006/0136051 A1 | 6/2006 | Furst et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2007/0005003 A1 | 1/2007 | Patterson et al. |
| 2007/0055144 A1 | 3/2007 | Neustadter et al. |
| 2007/0106108 A1 | 5/2007 | Hermann et al. |
| 2007/0270627 A1 | 11/2007 | Cutrer et al. |
| 2008/0057298 A1 | 3/2008 | Finley |
| 2008/0091055 A1 | 4/2008 | Nguyen et al. |
| 2008/0221384 A1 | 9/2008 | Chi Sing et al. |
| 2008/0221444 A1 | 9/2008 | Ritchie et al. |
| 2008/0228024 A1 | 9/2008 | Jones et al. |
| 2008/0287801 A1 | 11/2008 | Magnin et al. |
| 2009/0171157 A1 | 7/2009 | Diederich et al. |
| 2009/0188098 A1 | 7/2009 | Acosta et al. |

FOREIGN PATENT DOCUMENTS

| | | |
|---|---|---|
| EP | 0693293 B1 | 1/1996 |
| EP | 0719571 A2 | 7/1996 |
| EP | 0853957 B1 | 7/1998 |
| EP | 0867200 A2 | 9/1998 |
| EP | 1051990 A1 | 11/2000 |
| EP | 1070514 A1 | 1/2001 |
| EP | 1541188 A1 | 6/2005 |
| EP | 1618924 A1 | 1/2006 |
| JP | 10137250 A | 5/1998 |
| JP | 2001120561 A | 5/2001 |
| RU | 2177350 C2 | 12/2001 |
| WO | 9520241 A1 | 7/1995 |
| WO | 9712540 A1 | 4/1997 |
| WO | 9745053 A2 | 12/1997 |
| WO | 9815315 A1 | 4/1998 |
| WO | 9934869 A1 | 7/1999 |
| WO | 0158346 A1 | 8/2001 |
| WO | 0209599 A2 | 2/2002 |
| WO | 02069862 A1 | 9/2002 |
| WO | 2005039655 A1 | 5/2005 |
| WO | 2005039665 A1 | 5/2005 |
| WO | 2005067442 A2 | 7/2005 |
| WO | 2007027831 A1 | 3/2007 |
| WO | 2007143560 A2 | 12/2007 |

OTHER PUBLICATIONS

Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.

Devic, et al., "Advantages of Inflatable Multichannel Endorectal Applicator in the Neo-Adjuvant Treatment of Patients With Locally Advanced Rectal Cancer With HDR Brachytherapy", Journal of Applied Clinical Medical Physics, Spring 2005, pp. 44-49, vol. 6, No. 2.

Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.

Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.

Walton, R. J., "Therapeutic Uses of Radioactive Isotopes in the Royal Cancer Hospital", The British Journal of Radiology, 1950, pp. 559-599, William Heinemann, Publisher.

Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.

Low-Beer, B. V. A., "The Therapeutic Use of Radioactive Isotopes", "Practical Therapeutics", Dec. 1954, pp. 69-87, vol. X, No. 6.

Muller, J. H., "Radiotherapy of Bladder Cancer by Means of Rubber Balloons Filled In Situ With solutions of a Radioactive Isotope (Co60)", Cancer, A Journal of the American Cancer Society, Jul.-Aug. 1955, pp. 1035-1043, vol. 8, No. 4, J. B. Lippincott Company, Philidelphia.

Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.

Hewitt, C. B., et al., "Update on Intracavitary Radiation in the Treatment of Bladder Tumors", The Journal of Urology; Official Journal of The American Urological Association, Inc., 1981, pp. 323-325, vol. 126 September, The Williams & Wilkins Co.

Hieshima,G. B., et al. "A Detachable Balloon for Therapeutic Transcatheter Occlusions 1", Technical Notes, Jan. 1981, pp. 227-228, vol. 138.

Russel, A. H., et al, "Intracavitary Irradiation for Carcinoma of the Urinary Bladder: Rationale, Technique, And Preliminary Results", Int. J. Radiation Oncology. Phys,. 1984, pp. 215-219, vol. 10, Pergamon Press Ltd.

Yin, W., "Brachtherapy of Carcinoma of the Esophagus in China, 1970-1974 and 1982-1984", Brachytherapy HDR and LDR, May 4-6, 1989, pp. 52-56.

Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press plc.

Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.

Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.

Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.

Pernot, M., "Combined Surgery and Brachytherapy in the Treatment of Some Cancers of the Bladder (Partial Cystectomy and Interstitial Iridium-192)", Radiotherapy & Oncology, 1996, pp. 115-120, Elsevier Science Ireland Ltd.

Micheletti, E., et al., "High-Dose-Rate Brachytherapy for Poor-Prognosis, High-Grade Glioma: (Phase II) Preliminary Results", Tumori, 1996, pp. 339-344.

Lewis, J, et al., "Intracranial Brachytherapy Using A High Dose Rate Microselectron", Northern Centre for Cancer Treatement, Dept. Of Neurosciences, Regional Medical Physics Department, New Castle General Hospital, New Castle Upon Tyne, UK, p. 179.

Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.

Nag, S., et al., "Remote Controlled High Dose Rate Brachytherapy", Critical Reviews in Oncology/Hematology 22, 1996, pp. 127-150, Elsevier Science Ireland Ltd.

Sylvester, J., et al., "Interstitial Implantation Techniques in Prostate Cancer" Journal of Surgical Oncology 1997; 66: 65-75, Wiley-Liss, Inc.

Tan, L. T., et al., Radical Radiotherapy for Carcinoma of the Uterine Cervix Using External Beam Radiotherapy and A Single Line Source Brachytherapy Technique: The Clatterbridge Technique, The British Journal of Radiology, 70, date Dec. 1997, pp. 1252-1258.

Kuettel, M. R., et al., "Treatment of Female Urethral Carcinoma in Medically Inoperable Patients Using External Beam Irradiation and High Dose Rate Intracavitary Brachytherapy" The Journal of Urology, May 1997, pp. 1669-1671, vol. 157, The American Urological Association, Inc.

Slevin, N. J., et al., "Intracavitary Radiotherapy Boosting for Nasopharynx Cancer" The British Journal of Radiology, 70, Apr. 1997, pp. 412-414.

Sneed, P, K., et al., Interstitial Brachytherapy Procedures for Brain Tumors, Seminars in Surgical Oncology 1997; 13: 157-166, Wiley-Llss, Inc.

Dempsey, J. F., et al., "Dosimetric Properties of A Novel Brachytherapy Balloon Applicator For The Treatment Of Malignant Brain-Tumor Resection-Cavity Margins" Int. J. Radiation Oncology Biol. Phys., May 1998, pp. 421-429, vol. 42, No. 2, Elsevier.

Kolotas, C., et al., "CT Guided Interstitial High Dose Rate Brachytherapy for Recurrent Malignant Gliomas", The British Journal of Radiology, 72, (1999), pp. 805-808.

Demanes, D, J., et al., "The Use and Advantages Of A Multichannel Vaginal Cylinder In High-Dose-Rate Brachytherapy", Int. J. Radiation Oncology Biol. Phys., (1999), pp. 211-219, vol. 44, No. 1, Elsevier Science Inc.

Debicki, M. P., et al., "Localized Current Field Hyperthermia in Carcinoma of The Cervix: 3-D Computer Simulation Of SAR Distribution", International Journal of Hyperthermia, 1999, pp. 427-440, vol. 15, No. 5.

Garipagaoglu, M, et al., "Geometric and Dosimetric Variations of ICRU Bladder and Rectum Reference Points in Vaginal Cuff Brachytherapy Using Ovoids", Int. J. Radiation Oncology Biol. Phys.. 2004, pp. 1607-1615, Elsevier Inc.

Bowsher, W. G., et al., "Update on Urology-Prostate Cancer, 4-Treatment of Local Disease", European Journal of Surgical Oncology, 1995 pp. 679-682, vol. 21, No. 6.

Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.

Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.

Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, 50/3/MAR.

Hine, G. J., et al., "Isodose Measurements of Linear Radium Sources in Air and Water by Means of an Automatic Isodose Recorder",The American Journal of Roentgenology and Radium Therapy, 1950, pp. 989-998, vol. 64, No. 6, The Societies.

Walton, R. J., et al., Radioactive Solution (24Na and 82 Br) in the Treatment of Carcinoma of the Bladder:, British Medical Bulletin, 1952, pp. 158-165, Medical Dept., The British Council.

Marshall V. F., et al., "Current Clinical Problems Regarding Bladder Tumors", Symposium on Bladder Tumors, 1956, pp. 543-550, 9/3/May-Jun., J. B. Lippincott Co, Etc.

Hewitt, C. B., et al., "Intracavitary Radiation in the Treatment of Bladder Tumors", The Journal of Urology, vol. 107, Apr. 1972, pp. 603-606, The Williams & Wilkins Co.

Rotman, M., et al., "The Intracavitary Applicator in Relation To Complications Of Pelvic Radiation—The Ernst System", Int. J. Radiation Oncology Biol. Phys., 1978, pp. 951-956, vol. 4, Pergamon Press Inc.

Nag, S., et al., "The Future of High Dose Rate Brachytherapy", High Dose Rate Brachytherapy: A Textbook, 1994, pp. 447-453, Futura Publishing Company, Inc., Armonk, New York 10504.

Wang, C. C., "Carcinoma of the Nasopharynx", Radiation Therapy of Head and Neck Neoplasms, 1997, pp. 257-280, Chapter 10, Wiley-Liss, Inc.

Gaspar, L. E., et al., "Esophageal Brachytherapy", Principles and Practice of Brachytherapy, 1997, pp. 305-321, Futrua Publishing Company, Inc., Armouk, New York.

Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.

Akagi, Y, et al., "Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.

Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.

Stubbs, J. B., et al., "Preclinical Evaluation of a Novel Device for Delivering Brachytherapy to the Margins of Resected Brain Tumor Cavities", J. Neurosurg 96, Feb. 2002, pp. 335-343, vol. 96.

Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.

Paul V. Harper, "Some Therapeutic Applications of Radioisotopes", Journal of the Mississippi State Medical Association, Oct. 1966, vol. VII, pp. 526-533.

"Variable shield for radiation-therapy source wire and centering catheter", Research disclosure, Mason Publications, Hampshire, GB, vol. 438, No. 48, Oct. 2000, XP007126916.

Gregory K. Edmundson, et al., "Dosimetric Characteristics of the Mammosite RTS, a New Breast Brachytherapy Applicator", Int. J. Radiation Oncology Biol. Phys, vol. 52, No. 4, pp. 1132-1139, 2002.

Melvin A. Astrahan, PhD et al., "Optimization of Mammosite therapy", Int. J. Radiation Oncology Biol. Phys, vol. 58, No. 1, pp. 220-232, 2004.

Philip H. Gutin, et al., "A coaxial catheter system for afterloading radioactive sources for the interstitial irradiation of brain tumors", J. Neurosur, vol. 56, pp. 734-735, 1982.

R.D. Ashpole et al., "A New Technique of Brachytherapy for Malignant Gliomas with Caesium-137; A New Method Utilizing a Remote Afterloading system", Clinical Oncology, (1990).

Abstracts of the 11th International Conference on Brain tumor Research and Therapy Oct. 31-Nov. 3, 1995, Silverado Country Club and Resort, Napa, California, Journal of Neuro-Oncology 28:72, 1996.

Johannesen, T.B. et al, "Intracavity Fractioned Balloon Brachytherapy in Glioblastoma", Acta Neurochir (Wien) (1999) 141: 127-133.

XP007904995:retrieved from the internet: URL: http://www2.dupont.com/Teflon_Industrial/en_US/assets/downloads/h88800.pdf.

Cuttino, L. W., et al., "CT-Guided Multi-Catheter Insertion Technique for Partial Breast Brachytherapy: Reliable Target Coverage and Dose Homogeneity", Brachytherapy 4, 2005, pp. 10-17, Elsevier.

Glasgow, G. P., et al. "Remote Afterloading Technology", AAPM Report No. 41, 1993, pp. i-vi and 1-107, American Institute of Physics, Inc.

Hoshino, T., "Brain Tumor Research Center", Abstracts of the 11th Conference on Brain Tumor Research and Therapy, Journal of Neuro-Oncology 28, 1996, pp. 31-113.

* cited by examiner

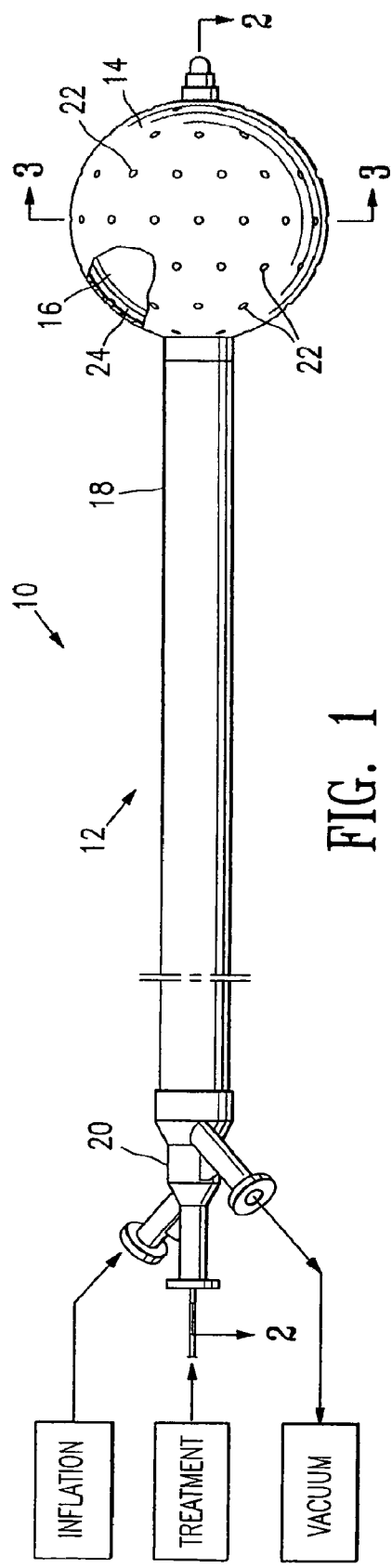
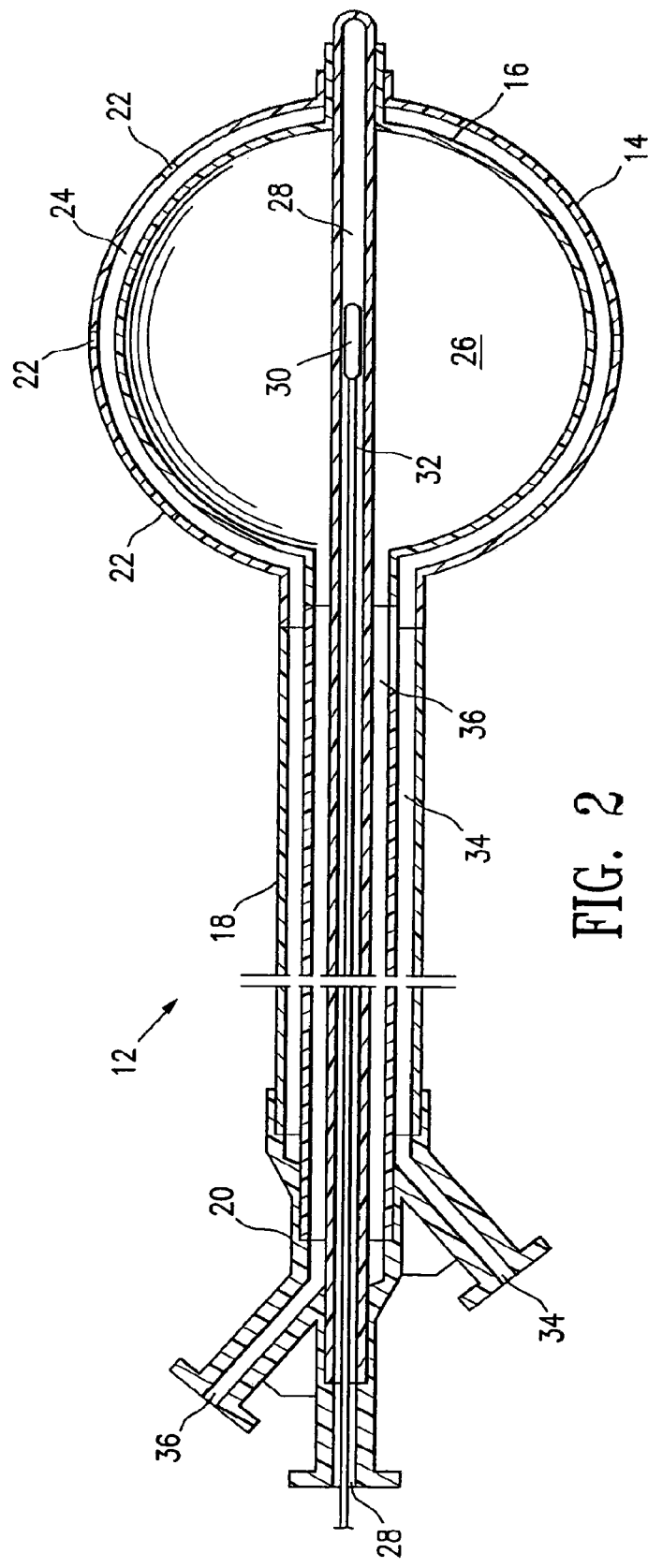

CATHETER ASSEMBLY FOR DELIVERING A RADIATION SOURCE INTO A BODY CAVITY

CROSS REFERENCE TO RELATED APPLICATIONS

This is a divisional application of U.S. patent application Ser. No. 11/155,789, entitled "VACUUM DEVICE AND METHOD FOR TREATING TISSUE ADJACENT A BODY CAVITY", filed Jun. 17, 2005, now U.S. Pat. No. 7,935,044 which is a continuation of U.S. patent application Ser. No. 10/290,002 filed Nov. 6, 2002, now U.S. Pat. No. 6,923,754, each of which is incorporated herein in its entirety by reference and from which priority is claimed.

FIELD OF THE INVENTION

This invention relates generally to the fields of medical treatment devices and methods. In particular, the invention relates to devices and methods for treating tissue surrounding a body cavity, such as a site from which cancerous, precancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 5,429,582 to Williams, U.S. Pat. No. 5,913,813 to Williams et al., U.S. Pat. No. 5,931,774 to Williams et al., U.S. Pat. No. 6,022,308 to Williams, U.S. Pat. No. 6,083,148 to Williams, and U.S. Pat. No. 6,413,204 to Winkler et al., the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Williams and coworkers describe implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The balloon may be filled with a treatment fluid delivered via a conduit from a receptacle, syringe, or other means, or may receive a solid radiation source placed within the balloon. Thus, radiation treatment may be applied to tissue adjacent the balloon by placing radioactive material such as radioactive "seeds" within the balloon, or by filling the balloon with a liquid or slurry containing radioactive material. Multiple treatments may be applied simultaneously. For example, radioactive seeds may be placed within the balloon effective to irradiate tissue surrounding the balloon, and the balloon filled with a hot fluid at the same time to provide thermal treatment. After a suitable time, the hot fluid and/or the radioactive seeds may be removed. Such treatments, combined or otherwise, may be repeated if desired.

For example, a "MammoSite® Radiation Therapy System" (MammoSite® RTS, Proxima Therapeutics, Inc., Alpharetta, Ga. 30005 USA) includes a balloon catheter with a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Iotrex®, Proxima Therapeutics, Inc.). The radiation source may be removed following each treatment session, or may remain in place as long as the balloon remains within the body cavity. Inflatable treatment delivery devices and systems, such as the MammoSite® RTS and similar devices and systems (e.g., GliaSite® RTS (Proxima Therapeutics, Inc.)), are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when all surrounding tissue regions receive the same dose of radiation, and where the radiation dosage received by more distant tissue is as small and as uniform as possible. However, tissue cavities typically are not uniform or regular in their sizes and shapes, so that differences in dosages applied to different regions of surrounding tissue, including "hot spots" and regions of relatively low dosage, often result from radiation treatment.

Thus, there is need in the art for improved devices and methods for delivering cancer treatment to a cavity site within a patient's body.

SUMMARY OF THE INVENTION

The invention provides assemblies, devices, systems, and methods for treating tissue adjacent a body cavity, such as a cavity formed by the removal of tissue from a patient. In methods and devices having features of the invention, vacuum is applied effective to draw tissue towards a treatment assembly placed within the body cavity. Assemblies and devices embodying features of the invention include a vacuum delivery element configured to apply a vacuum. A vacuum delivery element may include a vacuum conduit, and may further include a vacuum port. A vacuum delivery element may be configured to at least partially surround or enclose a treatment assembly. A treatment assembly may be configured to deliver a treatment, such as radiation therapy, chemotherapy, thermal therapy, or other treatment, to tissue adjacent a body cavity. A treatment assembly may include a treatment delivery element configured to contain a treatment material, such as a radioactive source. A treatment assembly may include an inflatable balloon, which may be disposed at least in part around a treatment delivery element.

Assemblies and devices embodying features of the invention may include a vacuum delivery element such as a sheath or a balloon configured to provide vacuum effective to apply suction to tissue adjacent the assemblies and devices. Vacuum delivery elements are preferably configured to apply suction to tissue adjacent a treatment delivery assemblies, such as an inflatable treatment delivery device. Suction is effective to draw surrounding tissue close to the surface of a treatment assembly, or to a vacuum delivery element (such as a sheath or balloon) at least partially surrounding or enclosing a treatment assembly, so as to shape the tissue lining the body cavity for optimal treatment. Treatment may be by, e.g., radiation therapy, chemotherapy, thermal therapy, or other treatment modality supplied by the device. A treatment assembly may include an inflatable treatment assembly such as an inner balloon assembly configured to be at least partly enclosed by a vacuum delivery element such as a sheath or balloon. A sheath may be configured to at least partly enclose a balloon temporarily, following placement over or around an inner balloon. A balloon may be configured to at least partly enclose a balloon permanently following placement over or around an inner balloon.

Devices may further include an enclosure assembly (which may comprise a sheath assembly or a balloon assembly) comprising a vacuum conduit and a fluid-permeable enclosure wall (e.g., a sheath wall or a balloon wall) configured to partly or completely enclose an inner balloon assembly. Such an enclosure assembly may be effective to provide vacuum and a vacuum path to an intermediate space outside the inner balloon assembly. An intermediate space may include a space disposed between the inner balloon assembly and a sheath assembly or an outer balloon assembly. The enclosure assembly is preferably operatively connected to a vacuum conduit effective to provide vacuum to the intermediate space. Systems having features of the invention include such devices and further include a vacuum source configured to operatively connect with the vacuum conduit. In embodiments of devices having features of the invention, a fluid-permeable enclosure wall may have a hole or multiple holes configured to allow passage of fluid, may be made with a fluid-permeable material, such as a fluid-permeable woven material, or may be otherwise fluid-permeable. The space between the inner balloon and the enclosure may be prevented from collapse, even in the presence of suction from a vacuum delivered via the vacuum conduit, by separation elements disposed on the inner balloon wall, or on the enclosure wall, or both. In alternative embodiments, separation elements disposed within an intermediate space may be independent of both the inner balloon wall and the enclosure wall.

An embodiment of a device for treating tissue adjacent a body cavity having features of the invention further comprises an inner balloon assembly, which may include or be operatively connected with an inflation conduit configured to allow passage of a fluid. Devices may also have an inner balloon comprising a distensible inner balloon wall defining an internal lumen. Such an inner balloon may be operatively connected to an inflation conduit so as to allow for passage of fluid through an inflation conduit and into the internal lumen so as to inflate the inner balloon with the fluid.

An enclosure wall preferably comprises a flexible material, more preferably an elastic flexible material, although in embodiments of the invention, an enclosure wall may comprise an inelastic flexible material. In embodiments of devices and systems having features of the invention, an enclosure wall comprises a polymer, such as biocompatible polymer, preferably a radiation-resistant polymer. Suitable polymers include polyolefins such as polyethylene and polypropylene, polyurethanes, polyester, polyvinylchloride, polystyrene, thermoplastic polymers such as C-Flex® (Consolidated Polymer Technologies, Inc., Clearwater Fla. 33762), block polymers such as Kraton™ (Kraton Polymers, Houston Tex. 77208), an ionomer such as Surlyn® (Dupont, Wilmington Del. 19880), nylon, latex rubber, and silicon rubber (e.g., SILASTIC™, Dow Corning, Midland, Mich.).

Devices and systems having features of the invention include inner balloon assemblies configured to enclose a treatment material, such as radioactive material, chemotherapeutic agents, and thermal treatment materials (e.g., materials having a temperature greater than about 37° C.).

The invention further provides methods for treating tissue adjacent a body cavity, comprising contacting tissue adjacent a body cavity with a sheath or an outer balloon having a fluid-permeable wall of a device having features of the invention; and applying a vacuum effective to enhance the contact between the fluid-permeable wall and the tissue. Further methods may include delivering inflation fluid to an inner balloon lumen via an inflation conduit to inflate a distensible balloon. In embodiments of the methods of the invention, the inner balloon assembly comprises a treatment assembly such as a Mammosite RTS or similar inflatable treatment delivery device. Methods may include placing a treatment material within the device, and may further include replacing the treatment material.

Body cavities are typically not uniform in size or regular in shape. Devices, systems and methods having features of the invention utilize suction to draw tissue against the device surface within a body cavity, insuring good contact between the device and body tissue and providing control over the spacing between tissue and the device, including control over the distance from the treatment material contained within the devices. Tissue lining a body cavity that is held close to, or in contact with, devices having features of the invention forms a uniform and controlled surface, unlike tissue lining a body cavity in which a prior art treatment device has been merely inserted, but which does not urge tissue into a desired orientation and position. The control over the distance, spacing, and amount of tissue contact provided by devices, systems and methods of the present invention offer the advantages of improved treatment tissue adjacent a body cavity. Such improvements may include more uniform dosing, reduction of "hot spots," shorter treatments due greater correlation between desired and actual dosages, and reduction in the number of locations receiving inadequate dosages.

The invention, in one form thereof, is directed to a catheter assembly for delivering a radiation source into a body cavity. The catheter assembly includes a catheter shaft having a distal end and a proximal end. An inflatable balloon is coupled to the catheter shaft between the distal end and the proximal end. A dose delivery lumen extends along the catheter shaft between the proximal end and the distal end. The dose delivery lumen is configured to receive the radiation source. A radioabsorptive portion is surrounded by the inflatable balloon.

The invention, in another form thereof, is directed to catheter assembly for delivering a radiation source into a body cavity. The catheter assembly includes a catheter shaft having a distal end and a proximal end. An inflatable balloon is coupled to the catheter shaft between the distal end and the proximal end. A dose delivery lumen extends between the inflatable balloon and the proximal end of the catheter shaft. A vent system includes one or more vents positioned along an outer surface of the inflatable balloon, and one or more vent lumens extending between the proximal end of the catheter shaft and the one or more vents.

The invention, in another form thereof, is directed to catheter assembly for delivering a radiation source into a body cavity. The catheter assembly includes an elongate shaft which has a proximal shaft portion, a distal shaft portion and a treatment location in the distal portion. A cavity filling member is located on a distal shaft portion surrounding the treatment location. The cavity filling member has an exterior surface. The cavity filling member is configured to at least partially fill the body cavity. At least one spacing member extends from the exterior surface of the cavity filling member.

BRIEF DESCRIPTION OF THE DRAWINGS

FIG. 1 is partially cut-away perspective view of a system embodying features of the invention shown configured to deliver a treatment within a cavity in a patient's body tissue while providing vacuum effective to urge tissue into contact with an outer balloon surface.

FIG. 2 is a longitudinal cross-sectional view of the system of FIG. 1 taken along line 2-2.

DETAILED DESCRIPTION OF THE INVENTION

Figure 4B:
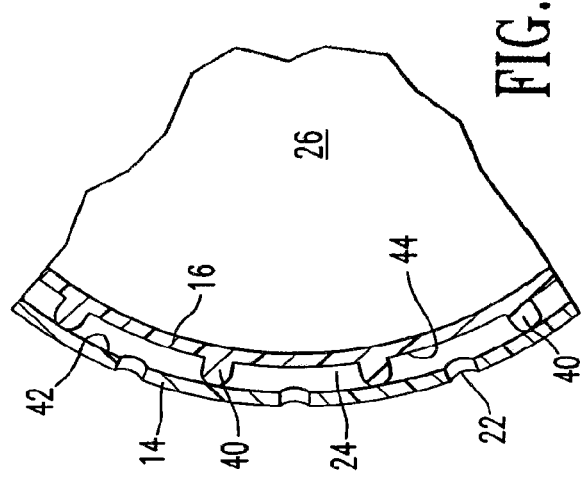
FIG. 4B is a cross-sectional view of the system of FIG. 1 showing a pie-shaped section of balloon walls between lines 4-4 for an embodiment in which an inner wall has stand-offs.

The present invention provides devices and methods for delivering a treatment, such as a cancer treatment, into a cavity within the body of an animal. For example, devices and methods having features of the invention may be used to deliver treatments into a biopsy site or into a cavity left after removal of cancerous tissue from within the body of a human patient. Vacuum is applied to tissue to enhance contact between a treatment delivery assembly within a body cavity and tissue surrounding the body cavity. A vacuum path around the treatment assembly is provided by devices, systems and methods embodying features of the invention. Vacuum may be applied to tissue via one, two, or multiple vacuum ports. A vacuum port may be a port in a vacuum delivery conduit, a hole in a sheath or balloon connected to a vacuum delivery conduit. A fluid permeable wall or portion of a fluid permeable wall may be effective to serve as a vacuum port.

FIG. 1 is a perspective view of a system 10 embodying features of the invention illustrating a device 12 having an outer balloon 14 enclosing an inner balloon 16 (shown in the cut-away portion of the illustration), a shaft 18 and connector 20. Outer balloon 14 comprises a sheath assembly around inner balloon 16. Outer balloon 14 is thus an example of an enclosure assembly, and forms an enclosure wall around inner balloon 16. Outer balloon 14 comprises at least in part a fluid permeable wall; as illustrated in FIG. 1, outer balloon 14 has holes 22 allowing fluid permeation into and out of balloon 14. In alternative embodiments, an outer balloon 14 may be made of woven or otherwise substantially continuous materials that are fluid permeable. In further embodiments, an enclosure wall or assembly such as an outer balloon may comprise a net, mesh, framework, or other discontinuous structure. Holes 22 (or fluid permeable material) allow fluids to pass through outer balloon 14 into intermediate space 24 disposed outside inner balloon 16. Intermediate space 24 provides a vacuum path adjacent inner balloon 16. Where at least a portion of outer balloon 14 is disposed adjacent inner balloon 16, intermediate space 24 is disposed between outer balloon 14 and inner balloon 16.

Inner balloon 16 defines an inner lumen 26, within which a delivery shaft 28 may be at least partially contained. As shown in FIG. 2, a treatment material 30 may be permanently or transiently disposed within delivery shaft 28. A probe 32 configured to move within delivery shaft 28 may be used to position treatment material 30, including to place treatment material 30 into and to retrieve placement material 30 from, within delivery shaft 28. A vacuum conduit 34 may be part of, or may be contained within, a shaft 18 and operatively connected to intermediate space 24. Shaft 18 may also include or contain an inflation conduit 36 configured to allow passage of inflation fluid into inner lumen 26. Passage of inflation fluid into inner lumen 26 is effective to inflate inner balloon 16. Inflation fluid may be any suitable fluid, either a gas or a liquid, and is typically inert. Inflation fluid, where a gas, may be, e.g., air, nitrogen, carbon dioxide or other gas. Inflation fluid, where a liquid, may be water, saline, mineral oil, or other liquid. In some embodiments, an inflation fluid may be effective to absorb radiation to, for example, moderate or adjust a dosage of radiation delivered to a patient's tissue from radioactive treatment material 30 contained within a delivery shaft 28.

Vacuum applied to intermediate space 24 is effective to deliver a treatment within a body cavity 38 within a patient's body effective to urge surrounding tissue into contact with at least a portion of the surface of the outer balloon 14.

The outer balloon 14 shown in FIGS. 1-5 is illustrated as a balloon that is configured to permanently or semi-permanently enclose inner balloon 16 or inner balloon assembly. Such an enclosure may be partial or complete. It will be understood that the outer surface of a device and of a system embodying features of the invention may also be a sheath 50 configured for deployment over and around an inner balloon assembly 14. In further embodiments, an enclosure may be, e.g. a net, mesh, framework, or other discontinuous structure.

Figure 3:
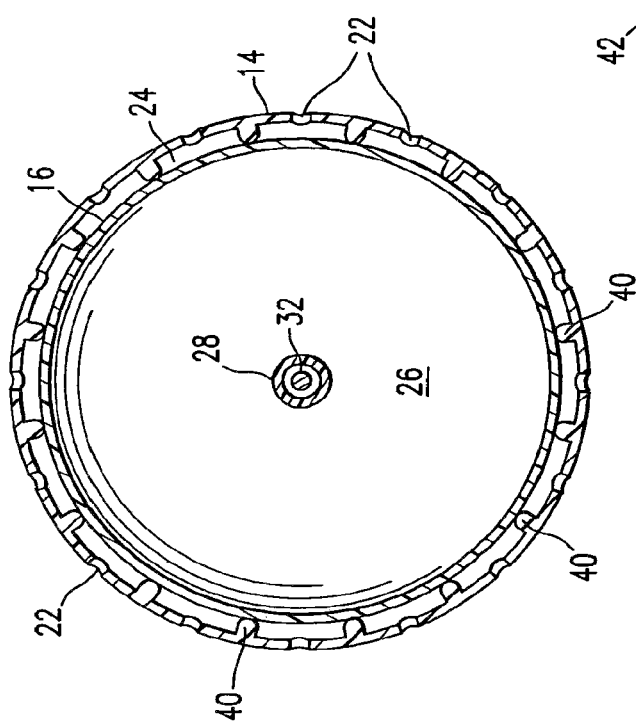
FIG. 3 is a transverse cross-sectional-view of the system of FIG. 1 taken along line 3-3.

FIG. 2 is a longitudinal cross-sectional view of the system of FIG. 1 taken along line 2-2 showing in cross section, for example, the relative positions of treatment material 30, an inner balloon 16, and an outer balloon 14 or sheath 50. FIG. 2 includes cross-sectional views of shaft 18 including views of delivery shaft 28, vacuum conduit 34 and inflation conduit 36. FIG. 3 is a transverse cross-sectional view of the system of FIG. 1 taken along line 3-3 showing outer balloon 14 and holes 22 therethrough, inner balloon 16 disposed within outer balloon 14, delivery shaft 28 and probe 32.

Figure 4A:
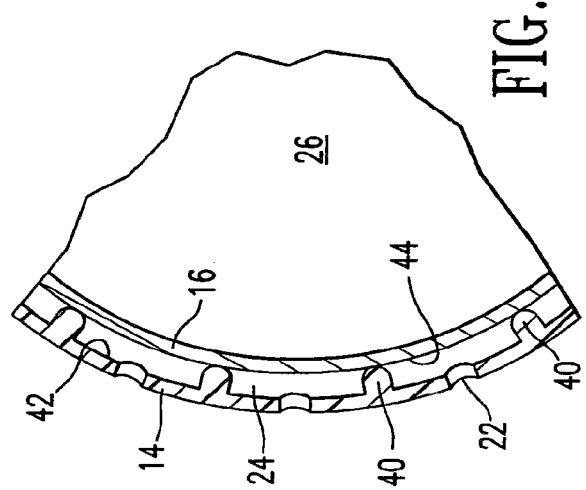
FIG. 4A is a cross-sectional view of a system of FIG. 1 showing a pie-shaped section of balloon walls between lines 4-4 for an embodiment in which an outer wall has stand-offs.

FIGS. 4A and 4B show portions of outer balloon 14 and inner balloon 16 as indicated in FIG. 1, including intermediate space 24 and spacers 40 which serve as separation elements effective to maintain patency of intermediate space 24 even under the influence of vacuum supplied via vacuum conduit 34. Spacers 40 may be part of outer balloon 14, or of inner balloon 16, or both. A spacer 40 may be a bump, knob, ridge, or other feature extending inwardly from an inner surface 42 of outer balloon 14, or extending outwardly from an outer surface 44 of outer balloon 14. In addition, or alternatively, a spacer 40 may be an object that is placed within intermediate space 24 and is separate from outer balloon 14 and inner balloon 16. For example, as shown in FIGS. 4A and 4B, spacers 40 may be stand-offs extending from an inner surface 42 of outer balloon 14 and from an outer surface 44 of outer balloon 14.

Figure 5A:
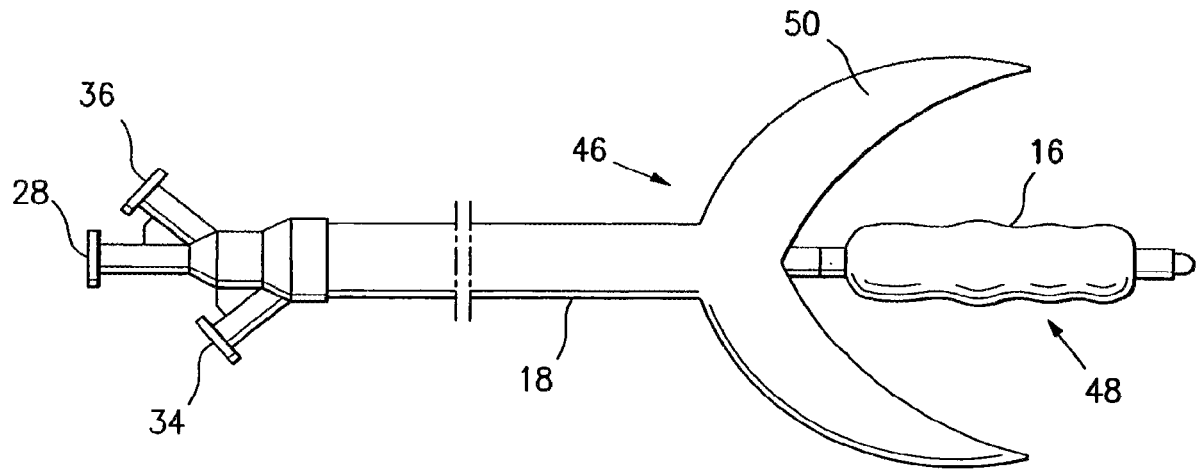
FIG. 5A shows a perspective view of a system embodying features of the invention in which an outer balloon assembly, in the form of a sheath, is being fitted over an inner balloon assembly.
Figure 5B:
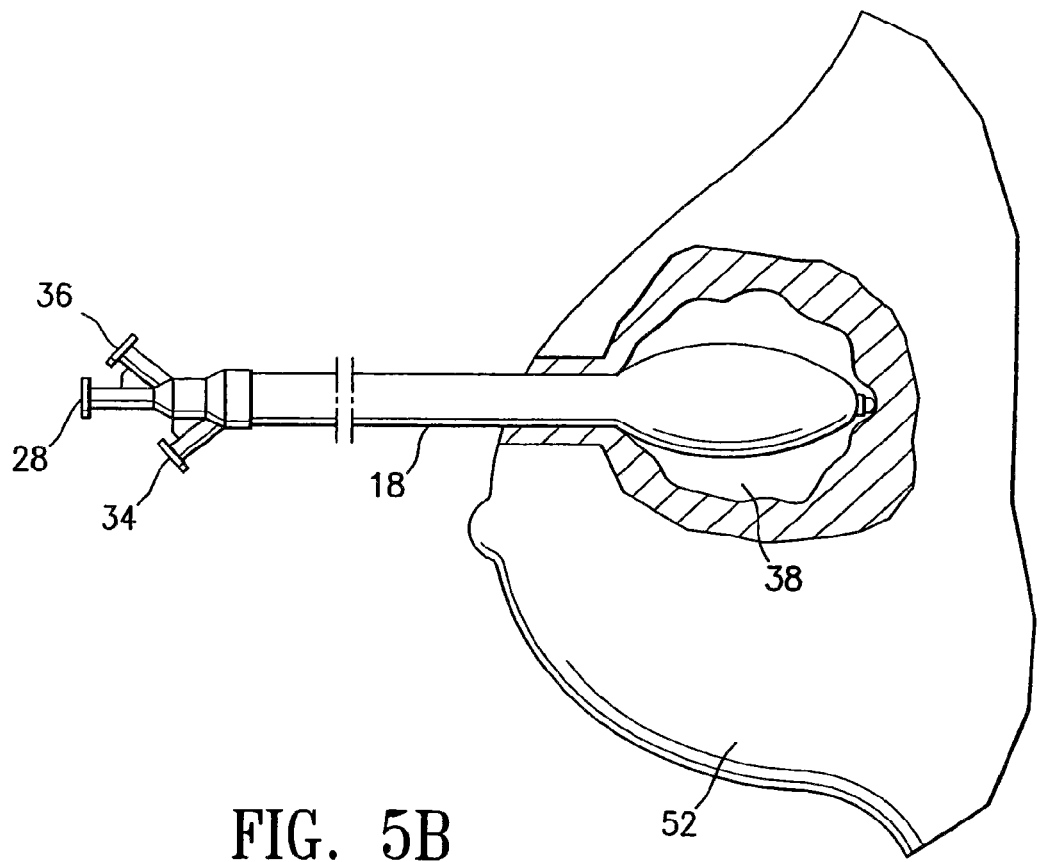
FIG. 5B shows a cross-sectional view of the assembled outer and inner balloon assemblies of FIG. 5A following placement into a cavity within a breast of a patient and before inflation of the inner balloon assembly.
Figure 5C:
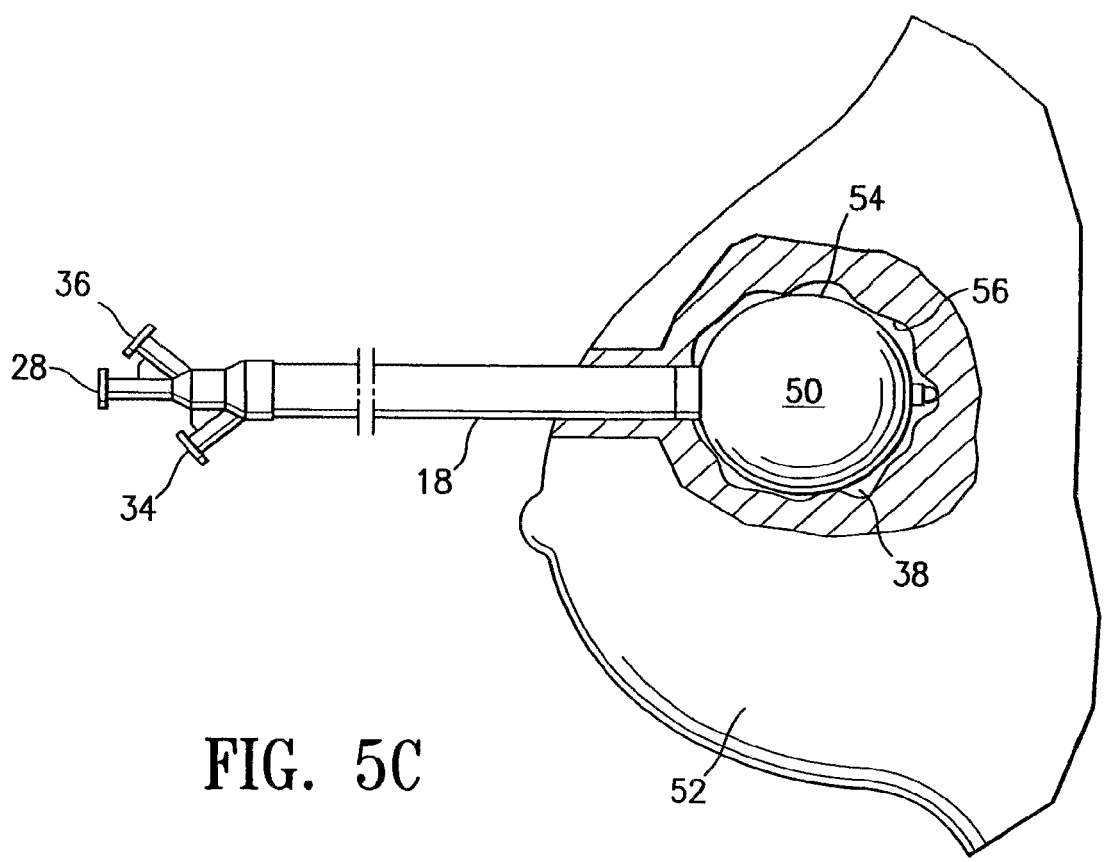
FIG. 5C shows a cross-sectional view of the assembled outer and inner balloon assemblies of FIG. 5A following inflation of the inner balloon assembly.

FIGS. 5A-5D illustrate the fitting of an outer balloon assembly 46 (including an outer balloon in the form of a sheath 50), over an inner balloon assembly 48 including an inner balloon 16. FIG. 5B shows the assembled outer 46 and inner 48 balloon assemblies of FIG. 6A following placement into a cavity 38 within a breast 52 of a patient and before inflation of the inner balloon assembly 48. In FIG. 5C, the inner balloon assembly 48 has been inflated by passage of inflation fluid through inflation conduit 36, pressing some parts of the outer surface 54 outer balloon assembly 46 into contact with portions of the inner surface 56 of body cavity 38. Note, however, that since most cavities 38 have irregular inner surfaces 56, there will typically be poor and intermittent contact between outer surface 54 of sheath 50 (or outer balloon 14 in alternative embodiments) and inner surface 56 of cavity 38, as shown in FIG. 5C.

Figure 5D:
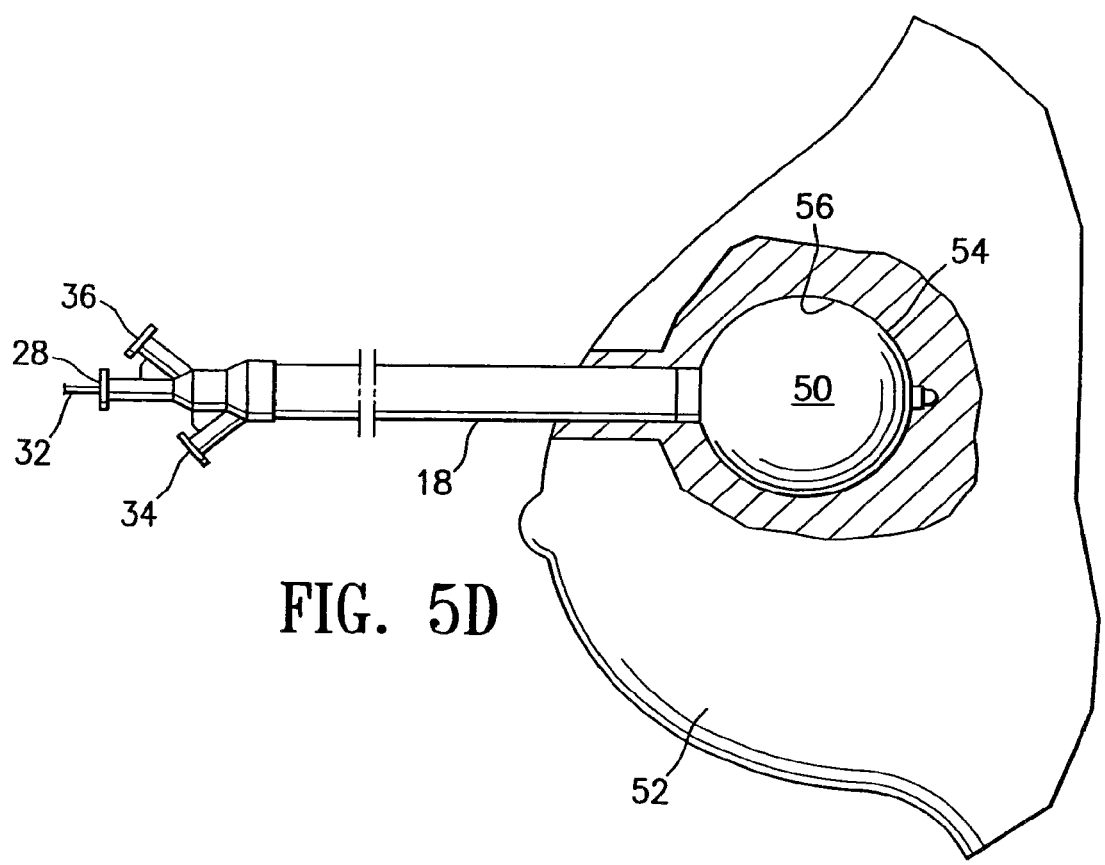
FIG. 5D shows a cross-sectional view of the assembled outer and inner balloon assemblies of FIG. 5A following application of vacuum to the lumen separating the inner balloon assembly and the outer balloon assembly, and after placement of a radioactive assembly within the inner balloon assembly.

FIG. 5D shows the assembled outer 46 and inner 48 balloon assemblies of FIG. 5A following application of vacuum via vacuum conduit 34 to the intermediate space 24 separating the inner balloon 16 and the sheath 50 (outer balloon 14). Treatment material 30 is in place within delivery shaft 28. Note that inner surface 56 of cavity 38 has been pulled into intimate contact with outer surface 54 of sheath 50. Such intimate contact configures inner surface 56 into an optimal configuration for the application of treatment by a treatment material 30. For example, radiation treatment by a radiation treatment material 30 is enhanced by proper positioning of adjacent tissue to provide proper irradiation. Irradiation levels may vary widely where the adjacent tissue of tissue cavity 38 is at different, irregular, or improper distances from a radiation source. Application of vacuum effective to draw tissue into better contact with device 12, e.g., into better contact with outer surface 54 of sheath 50, is effective to improve the delivery of radiation treatment from a radioactive treatment material 30.

Figure 6A:
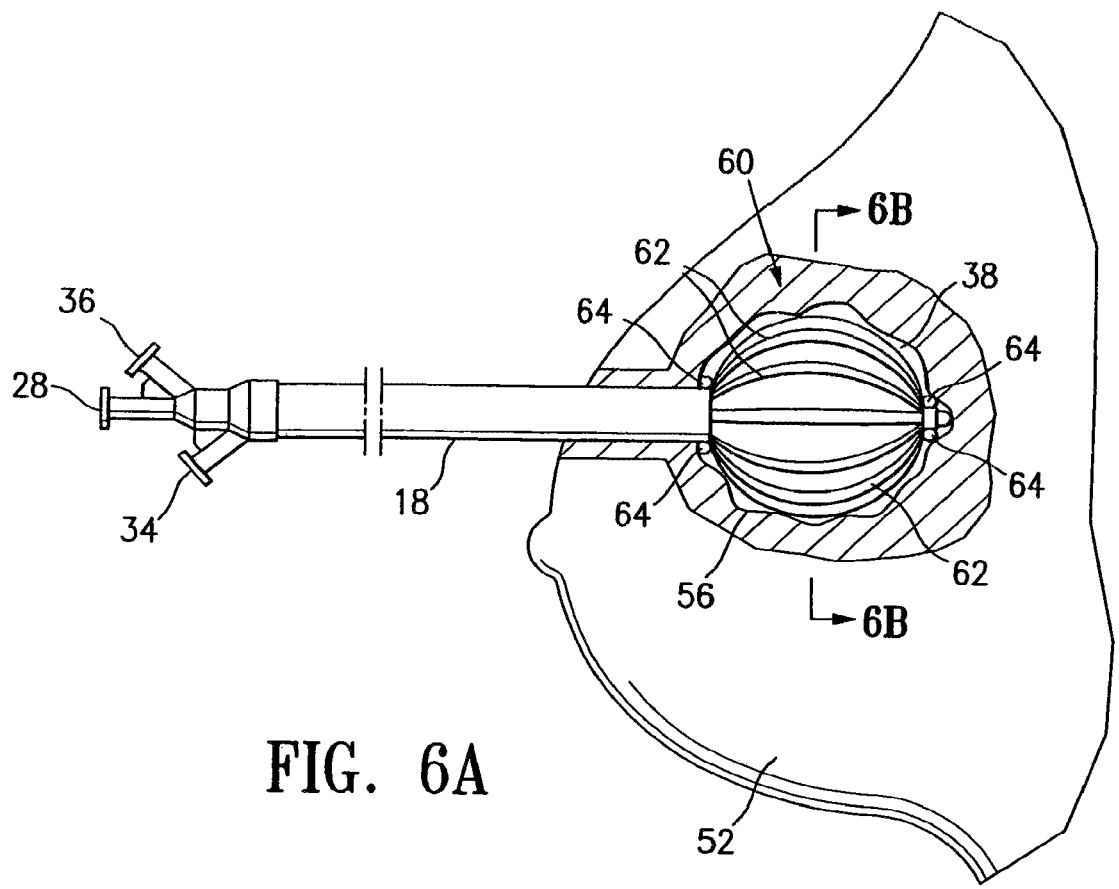
FIG. 6A is perspective view of a system embodying features of the invention including a vacuum delivery element configured to partly enclose an inner balloon assembly.
Figure 6B:
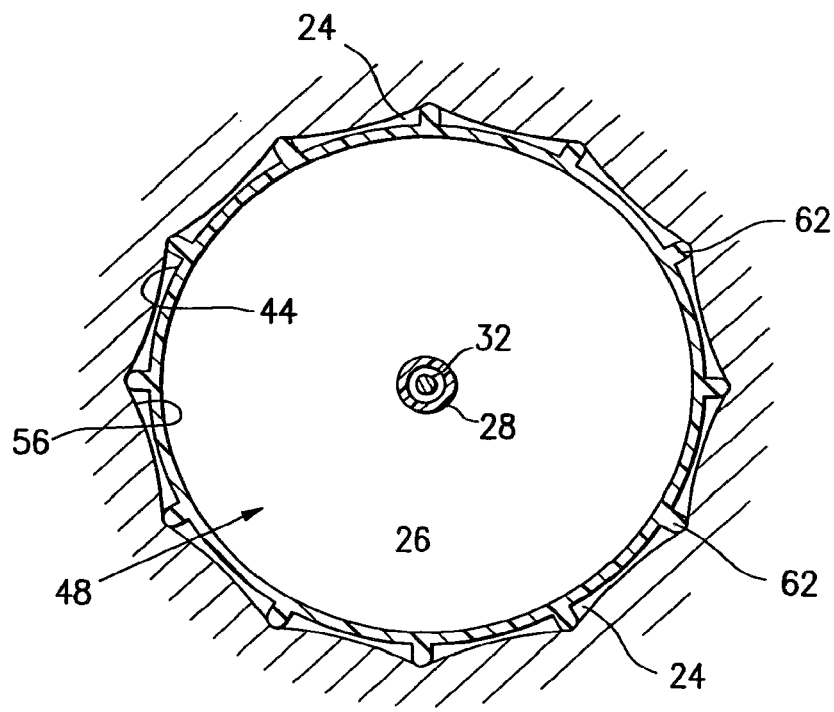
FIG. 6B is a cross-sectional view of the system of FIG. 6A taken along line 6B-6B.

FIG. 6A illustrates a system embodying features of the invention including a vacuum delivery element comprising an enclosure 60 having ribs 62 configured to partly enclose an inner balloon assembly 48. Vacuum is delivered to intermediate space 24 via vacuum ports 64 operatively connected to vacuum conduit 34. As shown in cross-section in FIG. 6B, ribs 62 serve as separation elements effective to provide vacuum paths in the intermediate space 24 between tissue surface 56 and outer surface 44 of inner balloon assembly 48.

Methods for treating tissue adjacent a body cavity 38 include methods for delivering a treatment to tissue adjacent a device 12 embodying features of the invention. For example, a method of treating tissue adjacent a body cavity 38 includes contacting tissue adjacent the body cavity 38 with a sheath 50 or an outer balloon 14, and applying a vacuum via vacuum conduit 34. The vacuum may be effective to draw adjacent tissue towards and into contact with a sheath 50 or an outer balloon 14, and so enhance the contact between the outer wall 54 and the tissue. Delivery of inflation fluid to an inner balloon 16 via an inflation conduit 36 to inflate inner balloon 16 is effective to enhance contact with adjacent tissue as well, serving to bring outer balloon 14 or sheath 50 closer to tissue than it would be in the absence of inflation of inner balloon 16. In preferred embodiments, the inner balloon assembly 48 comprises an inflatable treatment delivery device such as a Mammosite RTS (Proxima Therapeutics, Inc., Alpharetta, Ga. 30005) or similar device.

Methods further include placing a treatment material 30, such as a radiation source, within the device (e.g., by placement within a delivery shaft 28). A radiation source, such as a solid radiation source (e.g., a brachytherapy seeds) may be advanced into a delivery shaft 28 with a probe 32 or by other means. Other solid treatment materials 30 may similarly be advanced into a delivery shaft 28 with a probe 32 or by other means. A liquid radiation source (e.g., Iotrex®, Proxima Therapeutics, Inc., Alpharetta, Ga.) may be advanced into a delivery shaft 28 by fluid flow, under the influence of gravity, pressure applied by a syringe or other pressure source, or other means for delivering fluid into a space. Similarly, hot liquids and other liquid treatment materials 30 may be introduced into a delivery shaft 28 or an inner balloon 16 (via inflation conduit 36) under the influence of gravity, pressure applied by a syringe or other pressure source, or other means for delivering fluid into a space.

Some treatment regimens may include periodic or episodic treatment, in which radiation or other treatment is applied for a treatment period, and then the treatment is stopped for a recovery period. Such periodic or episodic treatments may be repeated, so that treatment is applied during a first treatment period, stopped during a first recovery period, and then treatment is re-applied for a second treatment period. Further treatment periods and recovery periods may also be used as necessary. Thus, methods may further include removal of a radiation source or other treatment material 30 from within a delivery shaft 28, and may further include replacing the treatment material 30.

Although a cavity 38 is typically an artificial cavity remaining after removal of tissue at biopsy, surgery, or other medical procedure, a body cavity may be a natural body cavity. For example, devices 12 may be inserted into a bladder for the treatment of bladder cancer. Application of suction is effective to enhance contact with a device 12 in such an example as well. Such enhanced contact may be effective to improve the delivery of radiation or other treatment, and may be effective to avoid "hot spots" (tissue regions receiving more radiation than is received by neighboring tissue regions) and is one of the important advantages provided by the present invention.

Treatment material 30 may include a chemotherapy agent effective to treat cancer or other disease condition of tissue surrounding a body cavity 38. In preferred embodiments, treatment material 30 includes a radiation source configured to delivery radiation to tissue adjacent a device 12.

Thus, treatment material 30 may include a radiation source which may be solid or liquid. A liquid radiation source may include, for example, a liquid containing a radioactive iodine isotope (e.g., $^{125}$I or $^{131}$I), a slurry of a solid isotope, e.g. $^{198}$AU, $^{90}$Y, $^{169}$Yb, or a gel containing a radioactive isotope. Liquid radiation sources are commercially available (e.g., from Iotrex®, Proxima Therapeutics, Inc., Alpharetta, Ga.).

A solid radiation source may include brachytherapy seeds or other solid radiation source used in radiation therapy, such as, for example a radioactive microsphere available from the 3M Company of St. Paul, Minn. A solid radioactive source can either be preloaded into a device 12 at the time of manufacture or may be loaded into the device 12 after placement into body cavity 38 of a distal portion of the device 12. Such distal portion preferably includes the outer balloon 14, inner balloon 16, and at least a portion of delivery shaft 28. Such a solid radioactive core configuration offers the advantage in that it allows a wider range of radionuclides than if one is limited to liquids. Solid radionuclides suitable for use with a delivery device embodying features of the present invention are currently generally available as brachytherapy radiation sources (e.g., I-Plant™, Med-Tec, Orange City Iowa).

In general, the amount of radiation desired by the physician is a certain minimum amount that is delivered to a site about 0-3 cm away from the wall of the body cavity 38 (e.g., from where a tumor has been excised). Vacuum applied to intermediate space 24 effects good contact between tissue surrounding body cavity 38 and the wall of the outer balloon 14 or sheath 50, promoting effective treatment delivery, such as delivery of radiation to surrounding tissue. It is desirable to keep the radiation in the region near the wall of the outer balloon 14 or sheath 50 as uniform as possible to prevent over-exposure to tissue at or near the reservoir wall. It is well known that the absorbed dose rate at a point exterior to a radioactive source is inversely proportional to the square of the distance between the radiation source and the target point. Thus, it is possible that the radiation dosage delivered to adjacent tissue may differ from that delivered to tissue disposed at more distal locations. In some instances, penetration of radiation to locations far from a device 12 is not desired. For example, in treating cancers such as bladder cancer, where the neoplastic tissue is generally located on the bladder surface, deep penetration is unnecessary and to be avoided.

An inflation fluid may also be a radiation absorbing fluid. For example, an inflation fluid may be an X-ray contrast agent as used in angiography, such as a Barium salt (e.g., barium sulfate), water, saline or other such fluid. A radiation-absorbing inflation fluid, which will surround a radiation source placed within delivery shaft 28, serves to moderate and control the delivery of radiation from the radiation source to surrounding tissue. Such moderation and control that is obtained with a radiation-absorbing inflation fluid may aid in avoiding the delivery of an excessive amount of radiation to some portions of the surrounding tissue.

Thus, in the absence of such a radiation-absorbing inflation fluid, it is possible in some instances that a radiation source sufficient to provide an effective dose at distances removed from a device 12, would expose tissue that is directly adjacent the wall of the outer balloon 14 or sheath 50 to an excessive radiation dose. Such excessive exposure to such tissue near to the device 12 may result in necrosis of healthy tissue necrosis.

Alternatively, an inflation fluid may contain radioactive elements, either as a liquid or slurry, so that the inner balloon 16 is filled with a source of radiation, providing a fairly uniform source of radiation that is distributed over the volume of the inner balloon 16. In such embodiments, an inflation fluid thus itself serves as a radiation source, thereby providing well-controlled amounts of radiation to surrounding tissue while minimizing irregularities in the dosages delivered to particular locations.

In embodiments of the invention in which an inflation fluid includes a radiation source, a delivery shaft 28 may contain a radiation absorptive material, so that, for example, less volume of radioactive material is required than if the entire volume of a device 12 were filled with radioactive material. Such a configuration may be advantageous where a profile exhibiting higher intensity at a tissue surface with lesser penetration is desired. Moreover, the outer balloon 14 need not be spherical, yet a uniform profile of radiation delivery is obtainable. Experiments reported in Williams U.S. Pat. No. 5,918,813 are described as showing that a steeper radial absorbed source gradient can be obtained using a radiation attenuation fluid in an inner chamber of a similar radiation deliver device than otherwise obtains with a device having only a single distensible chamber (as described in Williams U.S. Pat. No. 5,429,582).

What is claimed is:

1. A catheter assembly for delivering a radiation source into a body cavity, the catheter assembly comprising:
    a catheter shaft having a distal end and a proximal end, and an inflation conduit;
    an inflatable balloon coupled to the catheter shaft between the distal end and the proximal end, wherein the inflatable balloon defines an inner lumen that extends between the catheter shaft and the inflatable balloon, the inner lumen being in fluid communication with the inflation conduit;
    a dose delivery lumen extending along the catheter shaft between the proximal end and the distal end, the dose delivery lumen being configured to receive the radiation source and deliver the radiation source to a location within the catheter shaft that is surrounded by the inflatable balloon; and
    a radioabsorptive portion positioned in the inner lumen between the catheter shaft and the inflatable balloon, and surrounded by the inflatable balloon.

2. The catheter assembly of claim 1, comprising:
    an outer balloon positioned to surround the inflatable balloon; and
    a vent system, the vent system including:
    one or more vents positioned along an outer surface of the outer balloon; and
    one or more vent lumens associated with the catheter shaft, wherein the one or more vents are in fluid communication with the one or more vent lumens.

3. The catheter assembly of claim 1, wherein the catheter shaft has a vacuum lumen and at least one port in the catheter shaft proximal or distal to the inflatable balloon which is in fluid communication with the vacuum lumen to facilitate application of a vacuum within the body cavity.

4. A catheter assembly for delivering a radiation source into a body cavity, the catheter assembly comprising:
    a catheter shaft including a distal end and a proximal end;
    an inflatable balloon coupled to the catheter shaft between the distal end and the proximal end;
    a dose delivery lumen extending between the inflatable balloon and the proximal end of the catheter shaft; and
    a vent system including:
    one or more vents positioned along an outer surface of the inflatable balloon; and
    one or more vent lumens extending between the proximal end of the catheter shaft and the one or more vents.

5. The catheter assembly of claim 4, comprising an inflation lumen extending along the catheter shaft between the inflatable balloon and the proximal end.

6. The catheter assembly of claim 5, comprising a radioabsorptive portion surrounded by the inflatable balloon.

7. A catheter assembly for delivering a radiation source into a body cavity, the catheter assembly comprising:

an elongate shaft having a proximal shaft portion, a distal shaft portion and a treatment location in the distal shaft portion;

a cavity filling member located on the distal shaft portion surrounding the treatment location, the cavity filling member having an exterior surface, and the cavity filling member being configured to at least partially fill the body cavity; and at least one spacing member extending from the exterior surface of the cavity filling member.

8. The catheter assembly of claim 7, wherein the radiation source is provided in the treatment location in the distal shaft portion.

9. The catheter assembly of claim 7, wherein the elongate shaft has an inner lumen extending to the treatment location to facilitate delivery of the radiation source to the treatment location.

10. The catheter assembly of claim 7, wherein each of the at least one spacing member is a rib oriented longitudinally on the exterior surface of the cavity filling member.

11. The catheter assembly of claim 7, wherein the at least one spacing member is formed integrally with the cavity filling member.

12. The catheter assembly of claim 7, wherein the at least one spacing member is configured to provide space between the exterior surface of the cavity filling member and tissue lining the body cavity.

13. The catheter assembly of claim 7, wherein the cavity filling member is inflatable.

14. The catheter assembly of claim 13, wherein an inflation lumen extends through the elongate shaft to an interior portion of the inflatable cavity filling member to deliver inflation fluid to an interior portion of the cavity filling member to inflate the cavity filling member.

15. The catheter assembly of claim 14, wherein the inflatable cavity filling member is a balloon.

16. The catheter assembly of claim 14, wherein the inflation fluid is radioabsorptive.

17. The catheter assembly of claim 7, wherein the elongate shaft has a vacuum lumen and at least one port in the elongate shaft proximal or distal to the cavity filling member which is in fluid communication with the vacuum lumen to facilitate application of a vacuum within the body cavity.

18. The catheter assembly of claim 7, comprising a radioabsorptive portion surrounded by the cavity filling member.

* * * * *